United States Patent
Panin

(10) Patent No.: US 12,226,511 B2
(45) Date of Patent: Feb. 18, 2025

(54) DEODORANT COMPOSITION

(71) Applicant: HULKA S.R.L., Rovigo (IT)

(72) Inventor: Giorgio Panin, Rovigo (IT)

(73) Assignee: HULKA S.R.L., Rovigo (IT)

( * ) Notice: Subject to any disclaimer, the term of this patent is extended or adjusted under 35 U.S.C. 154(b) by 642 days.

(21) Appl. No.: 17/608,648

(22) PCT Filed: May 4, 2020

(86) PCT No.: PCT/EP2020/062259
§ 371 (c)(1),
(2) Date: Nov. 3, 2021

(87) PCT Pub. No.: WO2020/229209
PCT Pub. Date: Nov. 19, 2020

(65) Prior Publication Data
US 2022/0226224 A1    Jul. 21, 2022

(30) Foreign Application Priority Data

May 16, 2019   (IT) .................. 102019000006907

(51) Int. Cl.
| | | |
|---|---|---|
| *A61K 8/67* | (2006.01) | |
| *A61K 8/19* | (2006.01) | |
| *A61K 8/27* | (2006.01) | |
| *A61K 8/37* | (2006.01) | |
| *A61K 8/73* | (2006.01) | |
| *A61K 8/891* | (2006.01) | |
| *A61K 8/92* | (2006.01) | |
| *A61Q 15/00* | (2006.01) | |

(52) U.S. Cl.
CPC .............. *A61K 8/678* (2013.01); *A61K 8/19* (2013.01); *A61K 8/27* (2013.01); *A61K 8/375* (2013.01); *A61K 8/732* (2013.01); *A61K 8/891* (2013.01); *A61K 8/922* (2013.01); *A61Q 15/00* (2013.01); *A61K 2800/524* (2013.01)

(58) Field of Classification Search
CPC . A61K 8/678; A61K 8/19; A61K 8/27; A61K 8/375; A61K 8/732; A61K 8/891; A61K 8/922; A61K 2800/524; A61Q 15/00
See application file for complete search history.

(56) References Cited

U.S. PATENT DOCUMENTS

| | | | |
|---|---|---|---|
| 4,382,079 A * | 5/1983 | Marschner ........... | A61K 8/0229 424/59 |
| 5,662,937 A | 9/1997 | McCuaig | |
| 6,103,247 A * | 8/2000 | Boussouira ............. | A61P 39/06 424/617 |
| 7,736,632 B2 | 6/2010 | Gorman | |
| 9,399,006 B2 * | 7/2016 | Doering ................. | A61K 8/891 |
| 2008/0194715 A1 * | 8/2008 | Wendel ................... | A61Q 1/00 521/56 |
| 2008/0233060 A1 | 9/2008 | Grune | |
| 2009/0208438 A1 | 8/2009 | Gorman | |

FOREIGN PATENT DOCUMENTS

| | | |
|---|---|---|
| CA | 1196867 A | 11/1985 |
| DE | 102016225736 A1 | 6/2018 |
| WO | 2010080482 A2 | 7/2010 |
| WO | 2015121698 A1 | 8/2015 |

OTHER PUBLICATIONS

G. Panin, R. Strumia, and F. Ursini. "Topical a-Tocopherol Acetate in the Bulk Phase—Eight Years of Experience in Skin Treatment," Ann. N.Y. Acad. Sci. 1031: 443-447 (2004). (Year: 2004).*
Fact sheet on Spectrastat™ (available on the internet Apr. 10, 2015, downloaded Jun. 13, 2024 from https://www.ulprospector.com/en/na/PersonalCare/Detail/353/78344/Spectrastat. (Year: 2015).*
Mintel, Grapefruit Deodorant Cream, 2018, XP055651398.
Mintel, "Body Invisible Spray Powder", 2018, XP055651387.
Mintel, "Foot Cream", 2018, XP055651437.
International Search Report and Written Opinion for Corresponding International Application No. PCT/EP2020/062259 (10 Pages) (Jul. 10, 2020).

* cited by examiner

*Primary Examiner* — Michael P Cohen
(74) *Attorney, Agent, or Firm* — LUCAS & MERCANTI, LLP

(57) ABSTRACT

Cosmetic formulation with deodorant activity for topical application including vitamin E or an ester thereof, starch, sodium bicarbonate, zinc oxide and a cosmetically acceptable carrier is disclosed. The vitamin E ester is preferably alpha-tocopherol acetate, n-propionate or linoleate and the vitamin E or ester thereof and is present in an amount of 5-40% by weight of the weight of the formulation.

6 Claims, No Drawings

DEODORANT COMPOSITION

CROSS-REFERENCE TO RELATED APPLICATIONS

This application is a 371 of PCT/EP2020/062259, filed May 4, 2020, which claims the benefit of Italian Patent Application No. 102019000006907, filed May 16, 2019.

FIELD OF THE INVENTION

The present invention belongs to the cosmetic industry sector and concerns in particular a deodorant composition for personal hygiene, characterized by a high efficacy in controlling body odor and substantially free of skin irritation effects.

STATE OF THE ART

Body odor is due to the presence of fatty acids on the skin and foul-smelling substances produced by bacteria present on the skin. These foul-smelling substances are mainly organic molecules of different structure and functionality, such as amines, acids, alcohols, aldehydes, ketones, indoles, phenols, aromatic and polycyclic compounds.

Various compositions useful for body deodorization are known and also marketed, many of which contain aluminium salts and/or essential oils or perfuming agents, in order to cover body odor. However, these substances are likely to cause irritation not only to the skin but also to the respiratory tract, as well as to cause allergic responses.

Among the known deodorant compositions, those known from the following documents can be mentioned.

U.S. Pat. No. 5,662,937 describes a deodorant composition with prolonged action, comprising zinc oxide, citric acid and starch with an average particle size of about 14 micrometres and optionally a concentrate of vitamin E. In this patent a deodorant sold by the Israeli company Hlavin is mentioned with the name Lavilin and containing vaseline, potato starch, zinc oxide, *calendula* and *arnica* oils, vitamin E, ascorbyl palmitate, citric acid and perfume concentrate.

CA 1 196 867 describes a composition of stick deodorant, containing sodium stearate, propylene glycol, an antimicrobial agent, such as for example zinc phenolsulfonate or zinc ricinoleate, and optionally also vitamin E and sodium bicarbonate.

U.S. Pat. No. 7,736,632 describes a deodorant composition comprising shea butter, sodium bicarbonate, corn starch, cocoa butter, clary sage oil, benzoin tincture, coconut oil, lavender oil and possibly vitamin E up to a maximum content of 0.2% by weight.

WO 2010/80482 describes a cosmetic composition comprising a mixture of cycloalkylmethicones, which can be included in deodorants and which may comprise starch, vitamin E and zinc oxide.

WO 2015/121698 describes a deodorant preparation based on natural ingredients, with antibacterial and antifungal properties, containing coconut oil, an edible emulsifier, vitamin E and sodium bicarbonate.

US 2008/0233060 discloses high SPF transparent or translucent, cytoprotective, biodegradable, UV radiation resistant compositions. These compositions contain, among several other ingredients, starch, sodium bicarbonate, zinc oxide and vitamin E. Vitamin E is contained in an amount lower that 0.1% by weight of the total weight of the composition.

From the database GNPD MINTEL, 18 Jun. 2016, www.gndp.com, Database accession no. 5750711 a "Grapefruit Deodorant Cream" is known. Such cream contains tocopherol, tapioca starch, sodium bicarbonate and zinc oxide. The quantitative amounts of such components are not reported. Tocopherol is anyway the last but four among 18 listed components.

From the database GNPD MINTEL, 1 Aug. 2018, www.gndp.com, Database accession no. 5869849, a "Body Invisible Spray Powder" is known. Such spray powder contains tocopheryl acetate, tapioca starch, sodium bicarbonate and zinc oxide. The quantitative amounts of such components are not reported. Tocopherol is anyway the 20th among 27 listed components.

DE 102016225736A1 discloses an anhydrous cosmetic composition including a swelling, water-absorbing starch component, a scarcely swelling water-absorbing component, an odor-absorbing component and a deodorant active substance. Zinc oxide is mentioned among the odor-absorbing components.

The problem underlying the present invention was that of making available a new cosmetic formulation with deodorant activity able to reduce sweating and to prevent or reduce as much as possible the bad smell associated with sweating, without causing irritant or allergic effects of the skin and/or respiratory tract.

SUMMARY OF THE INVENTION

This problem has been solved, according to the invention, by a cosmetic formulation with deodorant activity for topical application comprising vitamin E or an ester thereof, starch, sodium bicarbonate, zinc oxide and a cosmetically acceptable vehicle, wherein vitamin E or an ester thereof is contained in an amount of 5-40%, preferably 15-35%, by weight of the weight of the formulation.

Vitamin E can be used in all its forms (tocopherols and tocotrienols, their isomers (alpha, beta, gamma, delta) and derivatives.

Preferably, the vitamin E ester is an alpha-tocopherol ester with a carboxylic acid of formula R—COOH, wherein R is an alkyl radical having from 1 to 19 carbon atoms, or an alkenyl or alkynyl radical having from 2 with 19 carbon atoms.

Preferably, the ester is alpha-tocopherol acetate, n-propionate or linoleate.

Preferably, the ester is alpha-tocopherol acetate.

Starch is preferably selected from the group comprising rice, corn, wheat, oats, *quinoa*, peas, *Pueraria lobata*, tapioca and barley starches and is advantageously rice starch.

The starch is preferably contained in an amount between 1 and 20% advantageously 5-18%, by weight of the total weight of the formulation.

The sodium bicarbonate is preferably contained in an amount comprised between 1 and 30%, advantageously 12-25%, by weight of the total weight of the formulation.

Zinc oxide is preferably contained in an amount between 1 and 10%, advantageously 2-5%, by weight of the total weight of the formulation.

The cosmetically acceptable vehicle can be selected from the siloxanes, in particular pentamer cyclomethicone, tetramer cyclomethicone, hexameter cyclomethicone, hexamethyldisiloxane, polydimethylsiloxane, disiloxane, trisiloxane and mixtures thereof. The use of a polydimethylsiloxane (dimethicone) is particularly preferred.

In another preferred embodiment, the aforementioned cosmetically acceptable vehicle is a hydrocarbon with a static viscosity less than or equal to 10 centistokes and a dynamic viscosity less than or equal to 9.8 mPa·s, measured at 25° C., and/or with a vapor pressure between 15 and 45 Pa measured at 25° C.

Preferably, the aforementioned hydrocarbon is selected in the group comprising hydrogenated polyisobutene (Hydrogenated Polyisobutene), hydrogenated polydecene (Hydrogenated Polydecene), mixtures of hydrogenated polyisobutene and/or hydrogenated polydecene with hydrogenated polyolefin (Hydrogenated $C_{6-14}$ Polyolefin), undecane (Undecane), isododecane (Isododecane), mixtures of isododecane with hydrogenated tetradecenylmethylpentadecene (Hydrogenated tetradecenyl/methylpentadecene) or with polyoxypropylene (3) myristyl ether neoheptanoate (PPG-3 Myristyl Ether Neoheptanoate), tridecane (Tridecane) and mixtures thereof.

In another embodiment, the cosmetically acceptable vehicle comprises water and at least one emulsifying agent and possibly at least one long chain alcohol ($C_{12}$-$C_{20}$) and at least one traditional or alternative preservative agent.

The emulsifying agent is preferably selected in the group comprising mono- and diglycerides of $C_{12}$-$C_{20}$ fatty acids and $C_{12}$-$C_{20}$ fatty acid esters with sorbitan.

A particularly preferred monoglyceride is glyceryl monostearate.

A particularly preferred long chain alcohol is cetylstearyl alcohol.

A particularly preferred preservative agent consists of an alternative-type preservative agent (i.e. an agent that does not fall within the list set out in Annex V of EC Regulation No. 1233/2009), which is a mixture of glycerin, caprilyl glycol and caprilhydroxamic acid, marketed under the name Spectrastat™ by the company Inolex.

Preferably the cosmetically acceptable carrier further comprises hydrogenated castor oil.

The cosmetically acceptable carrier may further contain thickening agents (e.g. carbomers) and pH regulators (e.g. triethanolamine).

The percentages reported in this disclosure, unless otherwise indicated, must be understood as percentages by weight on the total weight of formulation.

A particularly preferred formulation is the following:

| Alpha-tocopherol acetate | 25-30% |
| Sodium bicarbonate | 16-20% |
| Rice starch | 13-17% |
| Zinc oxide | 2-4% |
| Dimethicone | 25-30% |
| Hydrogenated castor oil | 7-9% |

DETAILED DESCRIPTION

The present invention will be further described with reference to some embodiments and to an efficacy evaluation test for an exemplary formulation in comparison with a known formulation.

Example 1

Deodorant in the Form of Hydrophobic Gel

| Alpha-tocopherol acetate | 28.1% |
| Sodium bicarbonate | 18.0% |
| Rice starch | 15.0% |
| Zinc oxide | 3.0% |
| Dimethicone | 27.9% |
| Hydrogenated castor oil | 8.0% |

The hydrogenated castor oil and the alpha-tocopherol acetate are heated to 85° C. and emulsified under vacuum inside a turboemulsifier with a rotation speed of 2200 rpm. Then, inside the turboemulsifier, with the turbine kept rotating, in the following order, zinc oxide, sodium bicarbonate and rice starch are added. Once complete homogenization is obtained, dimethicone is slowly introduced into the turboemulsifier under continuous homogenization, until the temperature drops to about 50° C. At this point, turbine cooling at 1300 rpm is started until reaching 40° C. The cooling is then continued, by operating the planetary agitator in place of the turbine, until reaching 30° C. At this point, the hydrophobic gel thus obtained is dosed inside plastic tubes.

Example 2

Stick Deodorant

| Glyceril monostearate SE | 5% |
| Cetyl stearyl alcohol 65/35 | 2% |
| Sorbitan Olivate | 3% |
| Caprylyl Glycol | 0.6% |
| Glycerin | 0.2% |
| Caprylhydroxamic acid | 0.2% |
| Alpha-tocopherol acetate | 20% |
| Water | 33% |
| Sodium bicarbonate | 18.0% |
| Rice starch | 15.0% |
| Zinc oxide | 3.0% |

The following are heated to 85° C.: alpha-tocopherol acetate, glyceryl monostearate, cetylstearyl alcohol, Sorbitan Olivate, Caprylyl Glycol, Glycerin and Caprylhydroxamic acid. The water is heated separately and, within a turboemulsifier, the two phases are turbine-emulsified with a rotation speed of 2200 rpm. Then, inside the turboemulsifier, with the turbine kept rotating, in the following order, zinc oxide, sodium bicarbonate and rice starch are added. At this point, turbine cooling is started at 1300 rpm until reaching 40° C. The cooling is then continued, by operating the planetary agitator in place of the turbine, until reaching 30° C. At this point, the emulsion thus obtained is dosed inside cases for stick deodorants.

Example 3

| Caprylyl Glycol | 0.75% |
| Glycerin | 0.15% |
| Caprylhydroxamic acid | 0.1% |
| Alpha-tocopherol acetate | 28.1% |
| Water | 30.4% |
| Sodium bicarbonate | 18.0% |
| Rice starch | 15.0% |
| Zinc oxide | 3.0% |
| Carbomer | 1.5% |
| Triethanolamine | 3% |

The water is dosed inside the turboemulsifier, the carbomer is added under stirring at 2000 rpm. Still under stirring, alpha-tocopherol acetate, caprylyl glycol, Caprylhydroxamic acid and glycerine are introduced into the turboemulsifier. Then zinc oxide, sodium bicarbonate and rice starch are introduced, in this order, into the turboemulsifier, with the turbine kept rotating. The pH is brought to neutrality with Triethanolamine, and mixing is performed for about 30 minutes. At this point, the emulsion thus obtained is dosed inside tubes.

The formulation of example 1 was subjected to an in vivo evaluation test of the deodorant efficacy in comparison with the Lavilin product, marketed by the Israeli company Hlavin, whose composition is shown below (INCI name):

RICINUS COMMUNIS (CASTOR) SEED OIL, TALC (CI77718), CI 77967 (ZINC OXIDE), POTATO STARCH MODIFIED, HYDROGENATED CASTOR OIL, COPERNICIA CERIFERA (CARNAUBA) WAX, GLYCINE SOJA (SOYBEAN) OIL, AQUAHYLYA, RECYCLED, TRIETHYL CITRATE, LACTOSE, LACTIC PROTEINUM (MILK PROTEIN), BIFIDA FERMENT LYSATE, CALENDULA OFFICINALIS FLOWER EXTRACT, PARFUM FRAGRANCE), PHENOXYETHANOL, O-CYMEN-5 OL, BENZYL ALCOHOLOLAN SANYA POTOLANA, ARNICA MONTANA.

The test was aimed at evaluating in vivo the sweat odor reducing effect of the two compared deodorant products, after the single application of the cosmetic products under examination. The evaluation of deodorant effectiveness of was performed according to a method based on the EEMCO guidelines on the SNIFF TEST (G E Pierard, P. Elsner, R. Marks, P. Masson, M. Paye, and the EEMCO Group, EEMCO Guidance for the Efficacy Assessment of Antiperspirants and Deodorants, Skin Pharmacology and Applied Skin Physiology 2003; 16: 324-342).

The test was performed on 20 healthy volunteers, selected after applying the inclusion/exclusion criteria.
Characteristics of the Volunteer Panel
  20 volunteers: 45% women, 55% men;
  Age: 21-66. Average age: 42.8;
  Volunteers developing body odor 1.5 (SNIFF TEST evaluation scale).
Pre-Selection Criteria for Volunteers:
  Good state of health.
  No skin pathologies.
  No ongoing topical drug treatments.
  Negative history of atopy.
  Exclusions: pregnant and breastfeeding women, minors.
  Commitment not to use other topical products in the area to be treated during the duration of the test and not to apply other products in the test areas for at least 7 days before the start of the test.

Volunteers were advised not to apply any perfume and/or other products in order not to create possible interference in the assessments, which could influence the test result.

Before starting the test, the deodorants under examination, a neutral non-perfumed soap and a cotton shirt, properly washed with a fragrance-free detergent, identified with a unique code for each volunteer, were delivered to each volunteer.

After careful ablution with a neutral fragrance-free soap, the deodorants were applied by an operator on each volunteer in a standardized way, so as to cover the entire axillary cavity.

The panel, made up of 20 volunteers, was randomly divided into two groups of 10 volunteers:
  PANEL I: deodorant A (formulation of example 1) was applied to 10 volunteers in the right armpit and deodorant B (Lavilin deodorant) in the left armpit;
  PANEL II: deodorant A was applied in the left armpit and deodorant B was applied in the right armpit of 10 volunteers.

The sweat odor assessment is performed by the 4 trained judges 24 hours after application;
T0—Application of the Product:

At the testing centre, the volunteer performed an accurate armpit ablution with a neutral, fragrance-free soap; the deodorants were applied by an operator, on each volunteer, in a standardized way so as to cover the entire axillary cavity, in particular, by applying a known quantity of deodorant cream.

At this point, the volunteer wears the adherent and unscented cotton T-shirt, especially washed with suitable fragrance-free detergents and undertakes to observe all the indications contained in the information note delivered to him.

T1—Evaluation 24 Hours after Application:

The volunteer hands over the shirt he has worn. An operator collects the shirts worn by the volunteers and prepares the shirts for judges' evaluation. The sweat odor assessment follows the score shown in the following Table 1.

TABLE 1

| SCORE SWEAT SMELL INTENSITY | SCORE |
|---|---|
| Absent | 0 |
| Slightly perceptible | 1 |
| Clearly perceptible | 2 |
| Moderate | 3 |
| Strong | 4 |
| Very strong | 5 |

The indicated score was expressed as the average of the judgments given by the 4 judges (2 men and 2 women), on each shirt.

According to the SNIFF TEST score, the effectiveness of the product is inversely proportional to the score obtained for the smell of sweat.

The following table shows the results of the judges' assessments for each volunteer.

| | | After 24 hours | | |
|---|---|---|---|---|
| Volunteer identification number | Sex | Age (years) | Formulation Example 1 | Lavilin |
| 1 | M | 21 | 0.8 | 0.3 |
| 2 | M | 22 | 1.0 | 1.0 |
| 3 | M | 39 | 1.0 | 2.3 |
| 4 | F | 41 | 0.0 | 0.8 |
| 5 | F | 36 | 0.0 | 0.3 |
| 6 | M | 66 | 0.3 | 0.5 |
| 7 | M | 47 | 0.3 | 0.5 |
| 8 | F | 38 | 0.5 | 0.5 |
| 9 | F | 37 | 1.0 | 1.3 |
| 10 | F | 38 | 0.8 | 1.0 |
| 11 | F | 36 | 1.5 | 1.5 |
| 12 | F | 44 | 1.3 | 0.8 |
| 13 | M | 52 | 0.8 | 0.3 |
| 14 | F | 44 | 1.5 | 1.8 |
| 15 | M | 36 | 0.8 | 2.0 |
| 16 | M | 36 | 0.5 | 0.3 |

-continued

After 24 hours

| Volunteer identification number | Sex | Age (years) | Formulation Example 1 | Lavilin |
|---|---|---|---|---|
| 17 | M | 65 | 0.8 | 1.5 |
| 18 | M | 58 | 0.0 | 0.0 |
| 19 | M | 63 | 0.5 | 0.3 |
| 20 | F | 37 | 1.3 | 1.8 |
| Average | | | 0.71 | 0.91 |
| Standard deviation | | | 0.47 | 0.68 |

The table above clearly shows that the formulation of Example 1 has a higher deodorant efficacy than that of the Lavilin product, being the known technique closest to the present invention.

The invention claimed is:

1. A cosmetic formulation with deodorant activity for topical application, comprising

| | |
|---|---|
| Alpha-tocopherol acetate | 25-30% |
| Sodium bicarbonate | 16-20% |
| Rice starch | 13-17% |
| Zinc oxide | 2-4% |
| Dimethicone | 25-30%, and |
| Hydrogenated castor oil | 7-9%. |

2. The cosmetic formulation according to claim 1, consisting of:

| | |
|---|---|
| Alpha-tocopherol acetate | 25-30% |
| Sodium bicarbonate | 16-20% |
| Rice starch | 13-17% |
| Zinc oxide | 2-4% |
| Dimethicone | 25-30% and |
| Hydrogenated castor oil | 7-9%. |

3. The cosmetic formulation according to claim 1, further comprising water and an emulsifying agent and optionally a preservative agent and/or a long chain ($C_{12}$-$C_{20}$) alcohol.

4. The cosmetic formulation according to claim 3, wherein said emulsifying agent is selected from the group consisting of mono- and diglycerides of $C_{12}$-$C_{20}$ fatty acids and sorbitan $C_{12}$-$C_{20}$ fatty acid esters.

5. The cosmetic formulation according to claim 3, wherein said emulsifying agent is glyceryl monostearate.

6. The cosmetic formulation according to claim 3, wherein said preservative agent is a mixture of glycerine, caprylyl glycol and caprylhydroxamic acid and said long chain alcohol is cetylstearyl alcohol.

* * * * *